United States Patent [19]
Müller et al.

[11] Patent Number: 5,817,837
[45] Date of Patent: Oct. 6, 1998

[54] TETRATHIAFULVALENE DERIVATIVE PRECURSORS, TETRATHIAFULVALENE DERIVATIVES, AND PROCESSES FOR PRODUCING THEM

[75] Inventors: Harald Dietmar Müller; Yoshinobu Ueba, both of Osaka, Japan

[73] Assignee: Sumitomo Electric Industries, Ltd., Osaka, Japan

[21] Appl. No.: 124,227

[22] Filed: Sep. 21, 1993

[30] Foreign Application Priority Data

Sep. 30, 1992 [JP] Japan .................................... 4-262348

[51] Int. Cl.$^6$ ................................................. C07D 339/06
[52] U.S. Cl. ................................................. 549/39; 549/36
[58] Field of Search ................................ 549/10, 11, 35, 549/36, 37, 39

[56] References Cited

U.S. PATENT DOCUMENTS

| | | | |
|---|---|---|---|
| 4,089,857 | 5/1978 | Engler et al. | 549/35 |
| 4,111,857 | 9/1978 | Engler et al. | 549/35 |
| 4,405,515 | 9/1983 | Engler et al. | 549/33 |
| 5,084,567 | 1/1992 | Mayer et al. | 540/1 |

FOREIGN PATENT DOCUMENTS

A-0204419  12/1986  European Pat. Off. .

OTHER PUBLICATIONS

Zeitschrift Fur Naturforschung, Teil B: Anorganische Chemie, Organische Chemie, Organische Chemie, vol. 46, No. 9, 1991.Tubingen DE, pp. 1269–1271, G. Papavassiliou et al 'Preparation of Some Bis(Alkylthio)–Bis–(Alkylseleno)Tetrathiafulvalene', p. 1269–p. 1270.

Chemical Abstracts, vol. 113, No. 28, 1990, Columbus, Ohio; abstract No. 58993u, E. Koslov et al, 'Tetrathiafulvalenes with Beta–halo– and Beta–Hydroxy–Ethylthio Groups', p. 687.

Chemical Abstracts, vol. 109, No. 28, 1988, Columbus, Ohio US; abstract No. 128969j, G. Abasbev et al, 'New Electron Donor. Bis(30XA–1,5–Dithiapentano)Terathiafulvalenes', p. 689.

Tetrahedron Letters, vol. 33, No. 2730, 30 Jun. 1992, Oxford GB, pp. 3923–3926, C. Gemmel et al, 'A Straightforward Approach to the Synthesis of Unsymmetrical Tetrathioalkyl Tetrathiafulvalene Derivatives'.

*Primary Examiner*—Deborah C. Lambkin
*Attorney, Agent, or Firm*—Sughrue, Mion, Zinn, Macpeak & Seas, PLLC

[57] ABSTRACT

A tetrathiafulvalene derivative precursor represented by formula (1), a tetrathiafulvalene derivative represented by formula (6), and processes for producing the tetrathiafulvalene derivative precursor and the tetrathiafulvalene derivative:

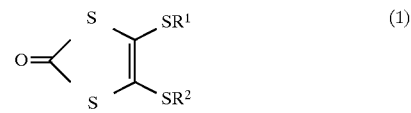

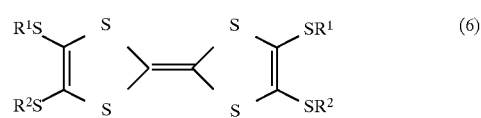

wherein $R^1$ and $R^2$ may be the same or different and represent organic groups that may be linked together to form a ring.

14 Claims, No Drawings

TETRATHIAFULVALENE DERIVATIVE PRECURSORS, TETRATHIAFULVALENE DERIVATIVES, AND PROCESSES FOR PRODUCING THEM

FIELD OF THE INVENTION

The present invention relates to tetrathiafulvalene derivatives having specified structures, as well as precursors thereof having specified structures, which are useful as materials for the synthesis of organic charge-transfer complexes that are expected to be used in such applications as organic conductors, organic superconductors, organic magnetic substances, organic electrochromic materials, organic electroluminescence materials and the like. The present invention also relates to processes useful for the production of various types of tetrathiafulvalene derivatives and precursors thereof, including the above structure-specified tetrathiafulvalene derivatives and their precursors.

BACKGROUND OF THE INVENTION

Attempts have been made to use tetrathiafulvalene derivatives as materials for the synthesis of organic charge-transfer complexes which are expected to be used in such applications as organic conductors, organic superconductors, organic magnetic substances, organic electrochromic materials, organic electroluminescence materials and the like. Great concern has been directed toward the development of new types of tetrathiafulvalene derivatives because of the limitation of practically available tetrathiafulvalene derivatives and of the demand for the development of new organic charge-transfer complexes.

As summarized in the following, there are several prior art processes for the synthesis of tetrathiafulvalene derivatives:

(i) Starting from the reduction of carbon disulfide with an alkali metal, a 1,3-dithiol-2-thione derivative is prepared. The thus prepared derivative is converted into a 1,3-dithiol-2-one derivative (dithiolone), and two molecules of the converted derivative are subjected to coupling to obtain a tetrathiafulvalene derivative. (A. Mizoe et al., *J. Chem. Soc. Chem. Commun.*, 1978, pp.18; G. Steimecke et al., *Phosphorus and Sulfur*, vol.7, pp.49–55 (1979); K. Hartke et al., *Chem. Ber.*, vol.113, pp.1898–1906 (1980)).

(ii) A tetrathiafulvalene derivative is prepared from 1,3,4,6-tetrathiapentalene-2,5-dione as a starting material making use of a phase-transfer catalyst. (R. R. Schumaker et al., *J. Org. Chem.*, vol.49, pp.564–566 (1984)).

(iii) A tetrathiafulvalene derivative is prepared from 1,2-ethanedithiol and chloroacetyl chloride as starting materials. (J. Larsen et al., *Synthesis*, pp. 134 (1989)).

The above process (i) has some disadvantages in that the reducing reaction of carbon disulfide with an alkali metal is apt to cause explosion, the process generates reaction by-products which are difficult to be removed, it requires a number of steps including conversion of a 1,3-dithiol-2-thion derivative into a 1,3-dithiol-2-one derivative, and the yield of a tetrathiafulvalene derivative as the product of interest is poor.

The above process (ii) also has a problem of causing low product yield, because it requires a laborious removal of a phase-transfer catalyst. Especially, since a column chromatography is used for the removal of the phase-transfer catalyst, a prolonged time of labor is required and the productivity becomes poor, resulting in difficulty in scale up.

The above process (iii) has also disadvantages in that it requires 5 steps for the completion of the synthesis, thus entailing a poor yield, and it has a narrow application range because it can be applied to the synthesis of bis(ethylenedithio)tetrathiafulvalene (BEDT-TTF) as one of the tetrathiafulvalene derivatives but hardly to the synthesis of other tetrathiafulvalene derivatives.

SUMMARY OF THE INVENTION

In view of the above, it therefore becomes an object of the present invention to provide novel tetrathiafulvalene derivatives and precursors thereof which are useful for the development of new organic charge-transfer complexes.

Another object of the present invention is to provide processes for the high yield production of high purity tetrathiafulvalene derivatives and their precursors, which can be applied not only to the above novel tetrathiafulvalene derivatives and precursors thereof but also to a broad range of other tetrathiafulvalene derivatives and their precursors, and which are free from the danger of causing explosion, do not generate hardly removable reaction by-products and have high productivity due to the absence of a laborious removal of catalysts.

Other objects and advantages of the present invention will be apparent from the following description.

The present invention relates to a tetrathiafulvalene derivative precursor represented by formula (1):

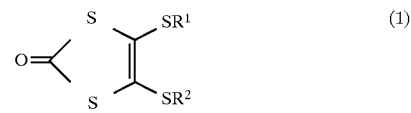

wherein $R^1$ and $R^2$ may be the same or different and represent organic groups that may be linked together to form a ring.

Examples of the tetrathiafulvalene derivative precursor represented by formula (1) include those represented by any one of formulae (2) to (5):

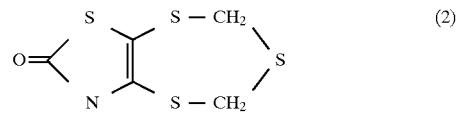

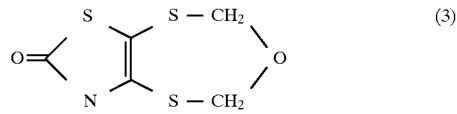

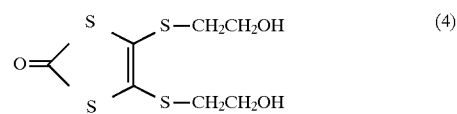

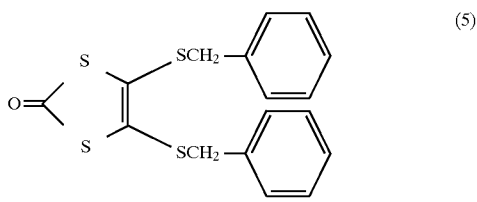

The present invention also relates to a tetrathiafulvalene derivative precursor represented by formula (6):

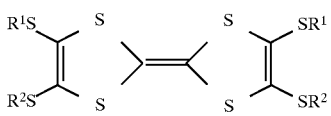

wherein $R^1$ and $R^2$ may be the same or different and represent organic groups that may be linked together to form a ring.

Examples of the tetrathiafulvalene derivative represented by formula (6) include those represented by any one of formulae (7) to (10):

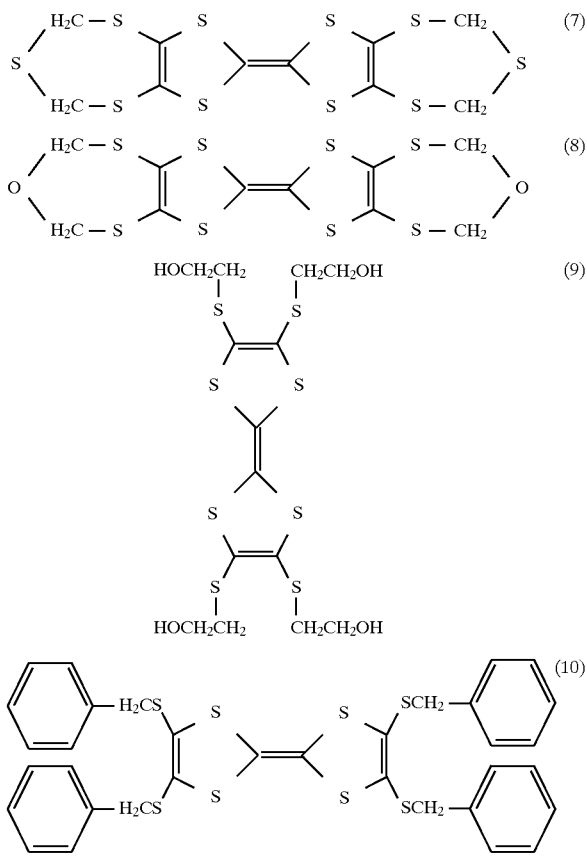

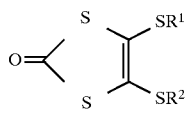

Each of these tetrathiafulvalene derivative precursors and tetrathiafulvalene derivatives of the present invention has a unique and novel structure which cannot be found in the prior art and is useful for the development of new organic charge-transfer complexes.

The present invention further relates to a process for producing a tetrathiafulvalene derivative precursor represented by formula (1):

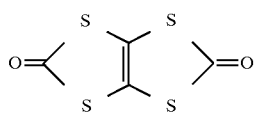

wherein $R^1$ and $R^2$ may be the same or different and represent organic groups that may be linked together to form a ring, the process comprising the steps of:
treating 1,3,4,6-tetrathiapentalene-2,5-dione at a temperature of 30° C. or lower in an alcohol solution containing an alkali metal methoxide in an inert atmosphere, thereby effecting selective cleavage of one of its rings to form 1,3-dithiol-2-one-4,5-dithiolate dianion; and allowing the 1,3-dithiol-2-one-4,5-dithiolate dianion to react with a compound having a monovalent or divalent organic group which corresponds to the organic groups represented by $R^1$ and $R^2$ in formula (1).

The present invention still further relates to a process for producing a tetrathiafulvalene derivative represented by formula (6):

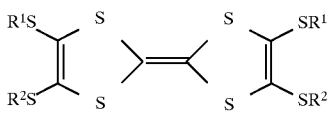

wherein $R^1$ and $R^2$ may be the same or different and represent organic groups that may be linked together to form a ring, the process comprising the steps of:
treating 1,3,4,6-tetrathiapentalene-2,5-dione at a temperature of 30° C. or lower in an alcohol solution containing an alkali metal methoxide in an inert atmosphere, thereby effecting selective cleavage of one of its rings to form 1,3-dithiol-2-one-4,5-dithiolate dianion;

allowing the 1,3-dithiol-2-one-4,5-dithiolate dianion to react with a compound having a monovalent or divalent organic group which corresponds to the organic groups represented by $R^1$ and $R^2$ in formula (6) to form a tetrathiafulvalene derivative precursor; and heating and stirring the tetrathiafulvalene derivative precursor in the presence of a trialkyl phosphite, thereby effecting coupling of two molecules of the precursor.

Examples of the organic groups represented by $R^1$ and $R^2$ in formulae (1) and (6) include an alkyl group (e.g., methyl, ethyl or the like), an aralkyl group (e.g., benzyl or the like), a hydroxyalkyl group, a trimethylsilylethoxymethyl group and the like. In the case where $R^1$ and $R^2$ are linked together to form a ring, examples thereof include an alkylene group (e.g., ethylene, propylene or the like), a dimethylenethio group, a dimethylene ether group and the like.

DETAILED DESCRIPTION OF THE INVENTION

With the aim of achieving the aforementioned objects, the inventors of the present invention have conducted intensive studies on the starting materials and reaction steps for the production of tetrathiafulvalene derivatives. As a result, it was found that dithiolone as a precursor of tetrathiafulvalene derivatives could be synthesized with a smaller number of steps than the prior art steps if one of the two rings of 1,3,4,6-tetrathiapentalene-2,5-dione represented by formula (11) could be cleaved selectively:

$$O=\!\!\bigg\langle\begin{array}{c}S\\S\end{array}\!\!\bigg\rangle\!\!\bigg\langle\begin{array}{c}S\\S\end{array}\!\!\bigg\rangle\!\!=\!O \qquad (11)$$

However, when 1,3,4,6-tetrathiapentalene-2,5-dione is subjected to a ring-opening reaction in the presence of a strong base such as sodium alkoxide, both of its two rings are cleaved as generally known, while nothing is known about a means to cleave one of them selectively.

In consequence, the present inventors have continued the studies further with the aim of finding a method for the selective one ring cleavage in 1,3,4,6-tetrathiapentalene-2,5-dione, and have found that one of the two rings can be cleaved selectively without generating hardly removable reaction by-products and with no danger of causing explosion, by a process in which an alkali metal alkoxide such as sodium methoxide or the like is made into a solution of about 1M in concentration by dissolving it in an alcohol such as methanol or the like and, in an inert atmosphere free from oxygen, moisture and the like, the alkoxide solution is added to 1,3,4,6-tetrathiapentalene-2,5-dione and allowed to undergo the ring-opening reaction for about 10 minutes under a relatively low temperature condition of 30° C. or below, especially at room temperature. The process of the present invention for the production of tetrathiafulvalene derivatives and precursors thereof, which include those of the present invention, has been accomplished on the basis of such efforts.

According to the production process of the present invention, as shown in the following reaction flow diagram, one of the two rings of 1,3,4,6-tetrathiapentalene-2,5-dione (11) is selectively cleaved to obtain 1,3-dithiol-2-one-4,5-dithiolate dianion (12), which is subsequently allowed to react with a compound having a monovalent or divalent organic group that corresponds to $R^1$ and $R^2$ in formula (1). In this way, a tetrathiafulvalene derivative precursor represented by formula (1) can be produced by a one-pot and one-step process without causing generation of hardly removable reaction by-products. Because of this, a tetrathiafulvalene derivative precursor can be produced in a high yield with a high purity in a short reaction time.

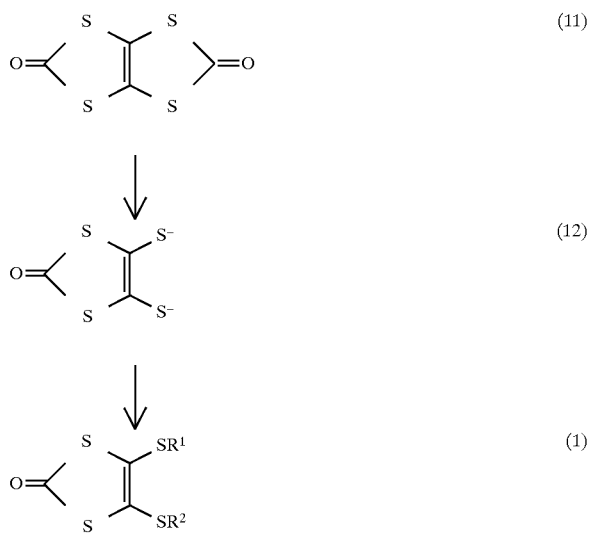

A tetrathiafulvalene derivative can be produced by employing the above precursor-producing step and a reaction step for the coupling of two molecules of the precursor, thereby rendering possible production of the tetrathiafulvalene derivative in a high yield with a high purity in a short reaction time.

In addition, the above production process can be carried out highly safely, because it does not involve explosion-causing dangerous reactions.

The above production process also has an advantage of a broad application range, because not only various types of prior art tetrathiafulvalene derivatives and their precursors but also novel tetrathiafulvalene derivatives and their precursors which cannot be produced by the prior art process, such as the tetrathiafulvalene derivative precursors of the present invention represented by formulae (2) to (5), the tetrathiafulvalene derivatives of the present invention represented by formulae (7) to (10) and the like, can be produced easily by the process of the present invention by selecting appropriate monovalent or divalent organic groups to be reacted with the 1,3-dithiol-2-one-4,5-dithiolate dianion (12).

The following describes the present invention in the order of the production steps.

Firstly, according to the production process of the tetrathiafulvalene derivative precursor according to the present invention, one of the two rings of 1,3,4,6-tetrathiapentalene-2,5-dione represented by formula (11) as the starting material is selectively cleaved to obtain 1,3-dithiol-2-one-4,5-dithiolate dianion represented by formula (12).

As described in the foregoing, the selective ring-opening reaction may be effected by a process in which an alkali metal alkoxide is made into a solution by dissolving it in the corresponding alcohol (e.g., $NaOCH_3$ in $CH_3OH$, $NaOC_2H_5$ in $C_2H_5OH$, etc.) and, in an inert atmosphere free from oxygen, moisture and the like, 1,3,4,6-tetrathiapentalene-2,5-dione (11) is added to the alkoxide solution and allowed to undergo the ring-opening reaction for about from 5 to 30 minutes, preferably from 5 to 20 minutes, more preferably from 8 to 12 minutes, under a relatively low temperature condition of 30° C. or below, preferably from 15 to 30° C., more preferaby from 18 to 25° C., particularly preferably from 20 to 23° C., especially at room temperature. When there is a possibility of causing an intense evolution of reaction heat, as it may be the case for large scale reaction, cooling with a water-bath (ca. 20° C.) is recommended.

The concentration of the solution of an alkali metal alkoxide is generally about 1M, preferably from 0.8 to 1.2M, and more preferably from 0.95 to 1.05M. Upon reaction, the amount of the alkali metal alkoxide is generally about 2 mol, preferably 1.8 to 2.2 mol, more preferably from 1.95 to 2.05 mol, per mol of 1,3,4,6-tetrathiapentalene-2,5-dione (11).

The term "room tempearture" used herein refers to such reaction conditions that external heating or cooling is not applied; in general the temperature range lies between from 20 to 25° C.

As alkali metal alkoxide, alkoxides of sodium and lower alcohols, such as sodium methoxide, sodium ethoxide and the like may be used, as well as other alkoxides of various alkali metals and alcohols. The alkoxide is generally used in an amount of 2 mols per 1 mol of 1,3,4,6-tetrathiapentalene-2,5-dione.

The product obtained after completion of the ring-opening reaction is next allowed to react with a compound containing a monovalent or divalent organic group which corresponds to $R^1$ and $R^2$ in formula (1) at room temperature for a period of approximately from 1 to 30 hours, preferably from 2 to 10 hours, and more preferably from 2 to 4 hours.

After completion of the reaction, the thus formed product is added to water and extracted with an organic solvent such as methylene chloride, and the solvent is removed under reduced pressure to obtain a crude product. The crude product is subsequently purified by conventional means such as recrystallization, reprecipitation and the like, to obtain the tetrathiafulvalene derivative precursor represented by formula (1).

As the compound containing the organic group corresponding to $R^1$ and $R^2$, a halide such as a chloride, a bromide, an iodide or the like may be used preferably as its reactivity with 1,3-dithiol-2-one-4,5-dithiolate dianion (12) is taken into consideration. A monohalide is used when the organic group is monovalent, or a dihalide when the organic group is divalent.

More specifically, when the organic group to be introduced as $R^1$ and $R^2$ is a monovalent group such as an alkyl group (e.g., methyl, ethyl or the like), an aralkyl group (e.g., benzyl or the like), a hydroxyalkyl group, or a trimethylsilylethoxymethyl group, a corresponding monohalide is used, which includes: an alkyl halide such as alkyl chloride, alkyl bromide, alkyl iodide or the like; an aralkyl halide such as aralkyl chloride, aralkyl bromide, aralkyl iodide or the like; and a trimethylsilylethoxymethyl halide such as trimethylsilylethoxymethyl chloride, trimethylsilylethoxymethyl bromide, trimethylsilylethoxymethyl iodide or the like. The monohalide is generally used in an amount of about 2 mols per 1 mol of 1,3-dithiol-2-one-4,5-dithiolate dianion.

When the organic group to be introduced as $R^1$ and $R^2$ is a divalent group which forms a ring by mutual binding, such as an alkylene group (e.g., ethylene, propylene or the like), a dimethylenethio group, or a dimethylene ether group, a corresponding dihalide is used, which includes: an alkylene dihalide such as alkylene dichloride, alkylene dibromide, alkylene diiodide or the like (e.g., $XCH_2—(CH_2)_n—CH_2X$, where X represents a halogen atom, and n represents an integer of 0 or more); and a dimethylenethiodihalide such as dimethylenethiodichloride, dimethylenethiodibromide, dimethylenethiodiiodide or the like. The dihalide is generally used in an amount of about 1 mol per 1 mol of 1,3-dithiol-2-one-4,5-dithiolate dianion.

When there is a possibility of causing too rapid progress in the reaction due to a high reactivity of the halide to be used, or the reaction is planed to be carried out in a large quantity, it is preferred from a safety point of view to suppress the reaction activity by diluting the reaction solution after completion of the ring cleavage with an alcohol or the like solvents and dissolving the halide in the same solvent prior to its addition to the diluted reaction solution.

Among tetrathiafulvalene derivative precursors represented by formula (1) which can be obtained by the above process for producing a tetrathiafulvalene derivative precursor of the present invention, tetrathiafulvalene derivative precursors of the present invention represented by formulae (2) to (5) are particularly useful as a starting material of the tetrathiafulvalene derivative of the present invention and for the development of new organic charge-transfer complexes:

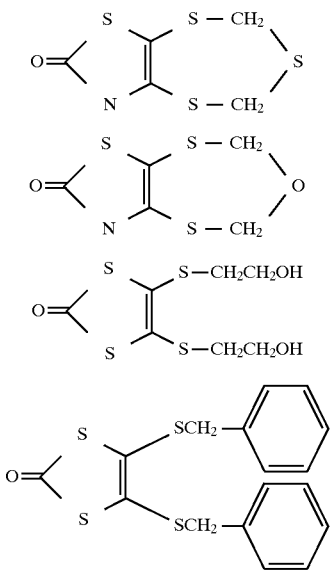

According to the process for producing tetrathiafulvalene derivatives of the present invention, a predetermined amount of the tetrathiafulvalene derivative precursor thus produced by the aforementioned precursor production process is firstly dissolved or dispersed in a purified trialkyl phosphite which is selected from various compounds including triethyl phosphite. The amount of the trialkyl phosphite to be used is not particularly limited but, in the case of triethyl phosphite for example, it is generally used in an amount of about 5 ml per one millimol of the tetrathiafulvalene derivative precursor.

By heating the solution or suspension thus prepared at approximately 100 to 120° C. with stirring, the coupling reaction of two molecules of the tetrathiafulvalene derivative precursor progresses, and reaction products containing a tetrathiafulvalene derivative represented by formula (6) as the product of interest are formed in the reaction solution as reddish yellow to reddish brown precipitate.

Thereafter, the thus formed precipitate is recovered by filtration, washed with a solvent such as methanol, and then subjected to purification by conventional means such as recrystallization, reprecipitation, column chromatography, sublimation and the like to obtain the tetrathiafulvalene derivative represented by formula (6).

Among tetrathiafulvalene derivatives represented by formula (6) which can be obtained by the above process for producing a tetrathiafulvalene derivative of the present invention, tetrathiafulvalene derivatives of the present invention represented by formulae (7) to (10) are novel compounds which renders possible development of new organic charge-transfer complexes:

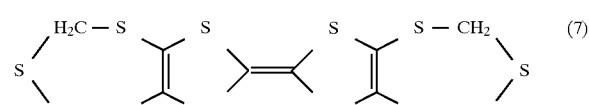

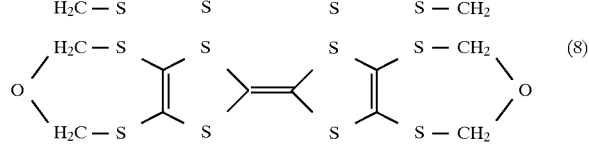

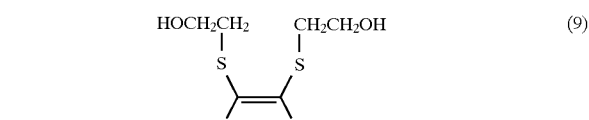

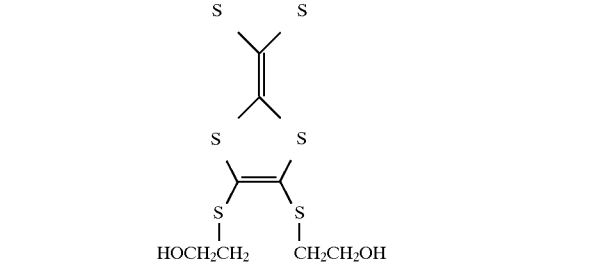

As has been described in the foregoing, according to the present invention, not only tetrathiafulvalene derivative precursors can be produced by merely a one-pot and one-step reaction system which does not generate hardly removable by-products and is free from danger of causing explosion and the like, but also tetrathiafulvalene derivatives can be produced from the tetrathiafulvalene derivative precursors by only a one-step reaction.

In consequence, in accordance with the processes of the present invention, tetrathiafulvalene derivative precursors and tetrathiafulvalene derivatives having higher purity than those produced by the prior art process can be produced by safer reaction systems and with higher yields in comparison with the prior art process, thus rendering possible production of tetrathiafulvalene derivatives in a large scale with low cost that cannot be attained by the prior art process.

In addition, according to the present invention, not only various types of known tetrathiafulvalene derivatives and their precursors but also novel tetrathiafulvalene derivatives and their precursors can be produced easily, thus rendering possible further development of new organic charge-transfer complexes using the tetrathiafulvalene derivatives as raw materials.

The following examples are provided to further illustrate the present invention. It is to be understood, however, that the examples are for purpose of illustration only and are not intended as a definition of the limits of the present invention.

EXAMPLE 1

(1) Synthesis of tetrathiafulvalene derivative precursor 9.6 ml of a standerized solution of sodium methoxide in methanol (concentration: 1 mol/l of methanol) was added at once to 1 g (4.8 mmol) of 1,3,4,6-tetrathiapentalene-2,5-dione, and the resulting dark green solution was stirred at room temperature for 10 minutes. To the resulting reaction solution was added 1.36 g (9.6 mmol) of methyl iodide all at once, followed by 2 hours of stirring at room temperature.

The thus prepared reaction solution was added to 150 ml of water, extracted three times with 50 ml of methylene chloride ($CH_2Cl$) and dried on magnesium sulfate ($MgSO_4$), followed by removing the solvent under a reduced pressure to obtain a crude product in a solid form. Thereafter, the crude product was recrystallized from ethanol to obtain 0.7 g of a purified product with a yield of 70%.

The thus purified product showed a melting point of 53 to 56° C. and was confirmed to be 4,5-dimethylthio-1,3-dithiol-2-one (molecular weight: 210.3) represented by formula (13):

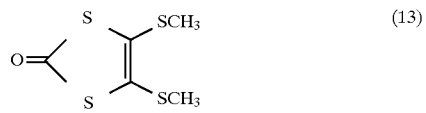
(13)

(2) Synthesis of tetrathiafulvalene derivative

A 2.1 g (10 mmol) portion of 4,5-dimethylthio-1,3-dithiol-2-one obtained in the above synthesis was dissolved in 50 ml of triethyl phosphite ($P(OC_2H_5)_3$) which has been freshly distilled and purified. The thus prepared solution was stirred for 3 hours at 100 to 120° C. Thereafter, the precipitate thus formed in the reaction solution was recovered by filtration, washed three times with 10 ml of methanol, dried, and then recrystallized from ethanol, thereby obtaining 0.37 g of a purified product with a yield of 50%.

When analyzed by elemental analysis (EA), it was confirmed that the thus purified product is a tetrathiafulvalene derivative represented by formula (14):

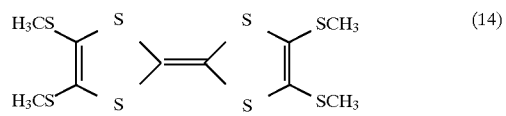
(14)

EXAMPLE 2

(1) Synthesis of tetrathiafulvalene derivative precursor

A crude product of precursor was obtained in a solid form by repeating the process for the synthesis of tetrathiafulvalene derivative precursor I as in Example 1 above except that 1.22 g (9.6 mmol) of benzyl chloride was used instead of methyl iodide. Thereafter, the crude product was dissolved in methylene chloride and reprecipitated with pentane to obtain 1.44 g of a purified product with a yield of 85 to 90%.

The thus purified product was subjected to melting point measurement, EA, infrared spectroscopic analysis (IR) using KBr tablet, mass spectrometry (MS) and nuclear magnetic resonance analysis ($^1$H-NMR), thereby obtaining the following results:

Melting point: 59 to 59.5° C. EA: calcd. (%); C=56.32, H=3.88 found (%); C=56.04, H=3.78 IR (KBr) v [cm$^{-1}$]: 1679 (vs, C=O), 1454, 1240, 898, 762, 692 MS (EI) m/z: 362 [M$^+$], 271, 243, 211, 91 $^1$H-NMR d [ppm vs TMS]: 3.87 (s, 4H, $CH_2$), 7.27 (m$_c$, 10H$_{arom}$)

On the basis of these results, the thus purified product was confirmed to be 4,5-dibenzylthio-1,3-dithiol-2-one (molecular weight: 362.5) represented by formula (5):

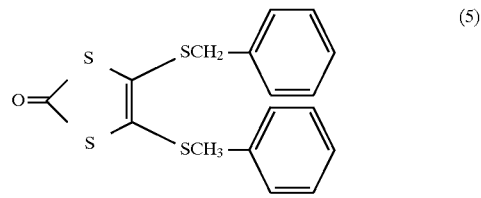
(5)

(2) Synthesis of tetrathiafulvalene derivative

The process for the synthesis of tetrathiafulvalene derivative as in Example 1 was repeated except that 3.6 g (10 mmol) of 4,5-dibenzylthio-1,3-dithiol-2-one obtained in the above synthesis I or II was used, to obtain 0.38 g of a purified product with a yield of 80%.

The thus purified product was analyzed by melting point measurement, EA, IR, MS and $^1$H-NMR, thereby obtaining the following results.

Melting point: 166.5 to 168.5° C. EA: calcd (%); C=58.92, H=4.07 found (%); C=58.26, H=3.83 IR (KBr) v [cm$^{-1}$]: 1493, 1451, 893, 768 (vs), 701 (vs), 660 MS (EI) m/z: 692 [M$^+$], 567, 536, 490, 444, 380, 357, 324, 212 $^1$H-NMR d [ppm vs TMS]: 3.85 (s, 8H, $CH_2$), 7.28 (m$_c$, 20H$_{arom}$)

On the basis of these results, the thus purified product was confirmed to be a tetrathiafulvalene derivative represented by formula (10):

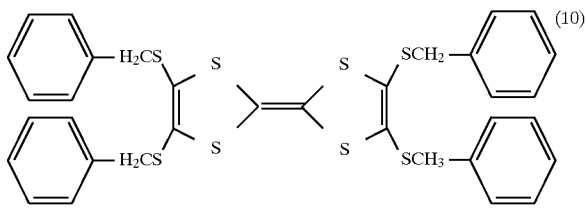
(10)

EXAMPLE 3

(1) Synthesis of tetrathiafulvalene derivative precursor

A crude product of precursor was obtained in a solid form by repeating the process for the synthesis of tetrathiafulvalene derivative precursor I as in Example 1 above except that 1.6 g (9.6 mmol) of trimethylsilylethoxymethyl chloride was used instead of methyl iodide. Thereafter, the crude product thus prepared was subjected to purification by a column chromatography using a silica gel carrier and a hexane/ethyl acetate mixture solvent (80/20) to obtain 1.36 g (yield: 60%) of 4,5-bis(trimethylsilylethoxymethyl)thio-1,3-dithiol-2-one (molecular weight: 442.81) represented by formula (15):

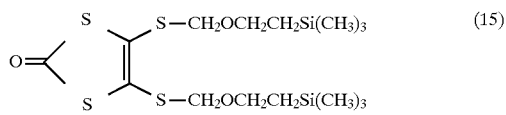

(2) Synthesis of tetrathiafulvalene derivative

The process for the synthesis of tetrathiafulvalene derivative as in Example 1 above was repeated except that 4.4 g (10 mmol) of 4,5-bis(trimethylsilylethoxymethyl)thio-1,3-dithiol-2-one obtained in the above synthesis I or II was used, to obtain 0.32 g (yield, 30%) of a crude tetrathiafulvalene derivative represented by formula (16):

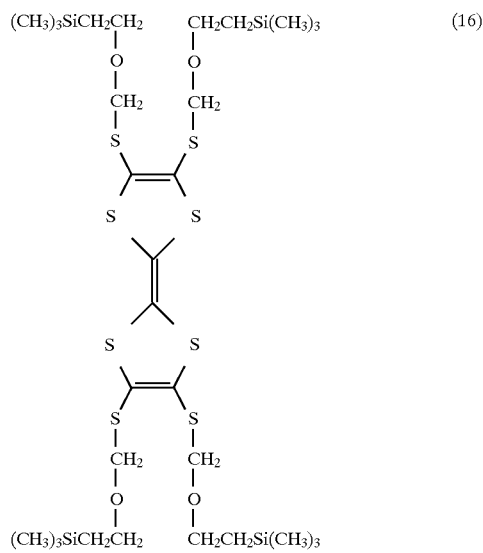

EXAMPLE 4

(1) Synthesis of tetrathiafulvalene derivative precursor

A crude product of precursor was obtained in a solid form by repeating the process for the synthesis of tetrathiafulvalene derivative precursor I as in Example 1 above except that 0.9 g (4.8 mmol) of ethylene dibromide (1,2-dibromoethane) was used instead of methyl iodide. Thereafter, the crude product was recrystallized from ethanol to obtain 0.5 g of a purified product with a yield of 45 to 50%.

The thus purified product showed a melting point of 127 to 128° C. when measured and was confirmed to be 4,5-ethylenedithio-1,3-dithiol-2-thione (molecular weight: 208.3) represented by formula (17):

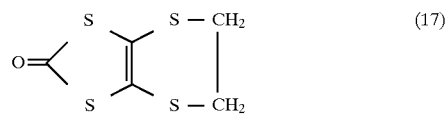

(2) Synthesis of tetrathiafulvalene derivative

The process for the synthesis of tetrathiafulvalene derivative as in Example 1 above was repeated except that 2.1 g (10 mmol) of 4,5-ethylenedithio-1,3-dithiol-2-one obtained in the above synthesis I or II was used, to obtain 1.6 g of a purified product with a yield of 85%.

Based on the results of EA, the thus purified product was confirmed to be a tetrathiafulvalene derivative (bisethylenedithio-tetrathiafulvalene, BEDT-TTF) represented by formula (18):

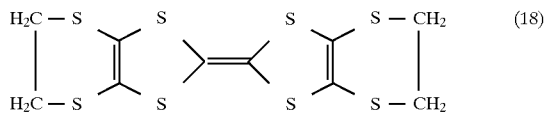

EXAMPLE 5

(1) Synthesis of tetrathiafulvalene derivative precursor

A crude product of precursor was obtained in a solid form by repeating the process for the synthesis of tetrathiafulvalene derivative precursor I as in Example 1 above except that 0.49 g (4.8 mmol) of propylene dibromide (1,3-dibromopropane) was used instead of methyl iodide. Thereafter, the crude product was recrystallized from ethanol to obtain 0.58 g of a purified product with a yield of 55%.

The thus purified product showed a melting point of 103 to 104° C. when measured and was confirmed to be 4,5-propylenedithio-1,3-dithiol-2-one (molecular weight: 222.3) represented by formula (19):

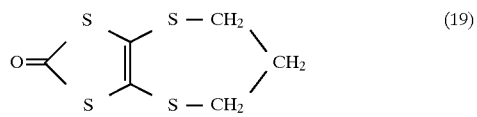

(2) Synthesis of tetrathiafulvalene derivative

The process for the synthesis of tetrathiafulvalene derivative as in Example 1 above was repeated except that 2.2 g (10 mmol) of 4,5-propylenedithio-1,3-dithiol-2-one obtained in the above synthesis I or II was used, to obtain 0.47 g of a purified product with a yield of 65%.

Based on the results of EA, it was confirmed that the thus purified product was a tetrathiafulvalene derivative (bis(propylenedithio)tetrathiafulvalene, BPDT-TTF) represented by formula (20):

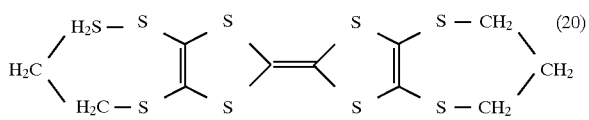

EXAMPLE 6

(1) Synthesis of tetrathiafulvalene derivative precursor

A crude product of precursor was obtained in a solid form by repeating the process for the synthesis of tetrathiafulvalene derivative precursor I as in Example 1 above except that 0.315 g (4.8 mmol) of dimethylenethiodichloride (bischloromethyl sulfide) was used instead of methyl iodide. Thereafter, the crude product was recrystallized from isopropyl alcohol to obtain 0.29 g of a purified product with a yield of 20 to 25%.

The thus purified product was subjected to melting point measurement, EA, IR, MS and $^1$H-NMR, thereby obtaining the following results.

Melting point: 197 to 198° C. EA: calcd (%); C=24.98, H=1.68 found (%); C=25.13, H=1.66 IR (KBr) ν [cm$^{-1}$]: 1682 (s), 1651 (vs), 1612 (s), 1357, 1223, 1162, 1128, 885, 856, 720 MS (EI) m/z: 240 [M$^+$], 180, 166, 88 $^1$H-NMR d [ppm vs TMS]: 4.00 (s, 4H)

On the basis of these results, the thus purified product was confirmed to be 4,5-(2-thiapropylene)-dithio-1,3-dithiol-2-one (molecular weight, 240.3) represented by formula (2):

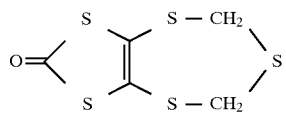

(2) Synthesis of tetrathiafulvalene derivative

The process for the synthesis of tetrathiafulvalene derivative as in Example 1 above was repeated except that 2.4 g (10 mmol) of 4,5-(2-thiapropylene)-dithio-1,3-dithiol-2-one obtained in the above synthesis I or II was used, to obtain 1.79 g of a purified product with a yield of 80%.

The thus purified product was analyzed by EA, IR and MS, thereby obtaining the following results:

EA: calcd (%); C=26.76, H=1.79 found (%); C=26.94, H=1.69 IR (KBr) ν [cm$^{-1}$]: 2958, 1364, 1218, 1164, 1126, 878, 852, 770, 722 MS (EI) m/z: 448 [M$^+$], 370, 268, 222, 180, 148, 88

On the basis of these results, the thus purified product was confirmed to be a tetrathiafulvalene derivative represented by formula (7):

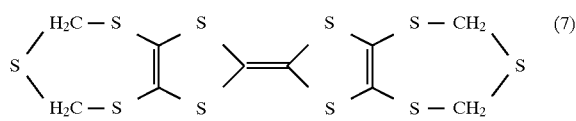

EXAMPLE 7

(1) Synthesis of tetrathiafulvalene derivative precursor

A crude product of precursor was obtained in a solid form by repeating the process for the synthesis of tetrathiafulvalene derivative precursor I as in Example 1 above except that 0.55 g (4.8 mmol) of dimethyleneoxydichloride (bischloromethyl ether) was used instead of methyl iodide. Thereafter, the crude product was recrystallized from isopropyl alcohol to obtain 0.5 g of a purified product with a yield of 50%.

The thus purified product was subjected to melting point measurement, EA, IR and $^1$H-NMR, thereby obtaining the following results:

Melting point: 159 to 161° C. EA: calcd (%); C=26.77, H=1.79 found (%); C=26.85, H=1.69 IR (KBr) ν [cm$^{-1}$]: 1682 (s), 1670 (vs, C=O), 1421, 1299, 1226, 1051 (s, C—O), 911 (s) $^1$H-NMR d [ppm vs TMS]: 4.89 (s, 4H)

On the basis of these results, the thus purified product was confirmed to be 4,5-(2-oxapropylene)-dithio-1,3-dithiol-2-one (molecular weight, 224.32) represented by formula (3):

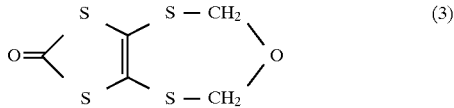

(2) Synthesis of tetrathiafulvalene derivative

The process for the synthesis of tetrathiafulvalene derivative as in Example 1 above was repeated except that 2.2 g (10 mmol) of 4,5-(2-oxapropylene)-dithio-1,3-dithiol-2-one obtained in the above synthesis I or II was used, to obtain 1.45 g of a purified product with a yield of 80%.

The thus purified product was analyzed by EA, IR and MS, thereby obtaining the following results.

EA: calcd (%); C=28.82, H=1.93 found (%); C=28.86, H=1.82 IR (Kbr) ν [cm$^{-1}$]: 2921, 1423, 1288, 1225, 1040, 974, 908, 773, 696, 664 MS (EI) m/z: 416 [M$^+$], 386, 355, 222, 178, 88

On the basis of these results, the thus purified product was confirmed to be a tetrathiafulvalene derivative represented by formula (8):

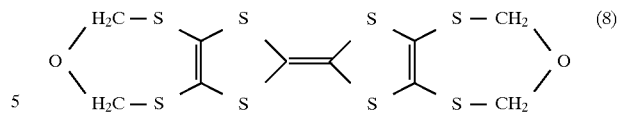

EXAMPLE 8

(1) Synthesis of tetrathiafulvalene derivative precursor

A crude product of precursor was obtained in a solid form by repeating the process for the synthesis of tetrathiafulvalene derivative precursor I as in Example 1 above except that 0.56 g (4.8 mmol) of bromoethanol was used instead of methyl iodide. Thereafter, the crude product was recrystallized from isopropyl alcohol to obtain 0.71 g of a purified product with a yield of 55%.

The thus purified product was subjected to melting point measurement, EA, IR, MS and $^1$H-NMR, thereby obtaining the following results.

Melting point: 90 to 92° C. EA: calcd (); C=31.09, H=3.73 found (%); C=31.09, H=3.43 IR (KBr) ν [cm$^{-1}$]: 1682 (s), 3278 (s, br, OH), 1675.5 (vs, C=O), 1407, 1076, 1055, 883, 793 MS (EI) m/z: 270 [M$^+$], 242, 199, 149, 121, 45 $^1$H-NMR d [ppm vs TMS]: 3.05 (m$_c$, 4H, —SCH$_2$), 3.8 (m$_c$, 4H, HOCH$_2$)

On the basis of these results, the thus purified product was confirmed to be 4,5-bis(hydroxyethyl)-dithio-1,3-dithiol-2-one (molecular weight, 270.39) represented by formula (4):

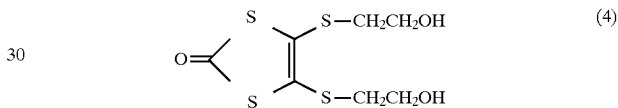

(2) Synthesis of tetrathiafulvalene derivative

The process for the synthesis of tetrathiafulvalene derivative as in Example 1 above was repeated except that 2.7 g (10 mmol) of 4,5-bis(hydroxyethyl)-dithio-1,3-dithiol-2-one obtained in the above synthesis I or II was used, to obtain a tetrathiafulvalene derivative represented by formula (9):

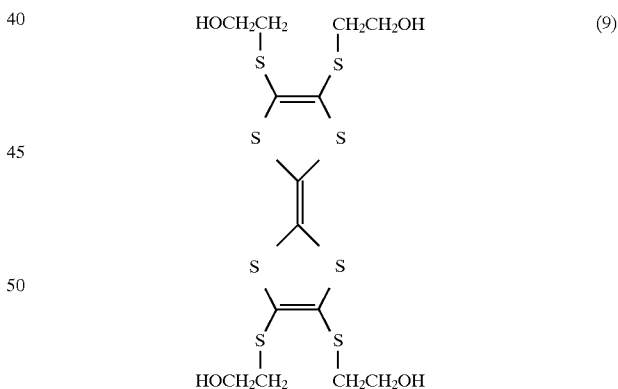

Thus, as has been described in the foregoing in detail, each of the tetrathiafulvalene derivatives and their precursors of the present invention has a novel structure which cannot be found in the prior art and is useful for the development of new organic charge-transfer complexes.

According to the process for the production of tetrathiafulvalene derivative precursors of the present invention, tetrathiafulvalene derivative precursors can be produced by merely a one-pot and one-step reaction system which does not generates hardly removable by-products and is free from danger of causing explosion and the like. Also, according to the process for the production of tetrathiafulvalene derivatives of the present invention, tetrathiafulvalene derivatives can be produced from the tetrathiafulvalene derivative precursors by only a one-step reaction.

In consequence, in accordance with the present invention, tetrathiafulvalene derivative precursors and tetrathiafulvalene derivatives having higher purity than those produced by the prior art process can be produced by safer reaction systems and with higher yields in comparison with the prior art process, thus rendering possible production of tetrathiafulvalene derivatives in a large scale with low cost that cannot be attained by the prior art process.

The production process of the present invention, therefore, has a high industrial utilization value as a means for the low cost and large scale production of tetrathiafulvalene derivatives which are expected to be used in such applications as organic conductors, organic superconductors, organic magnetic substances, organic electrochromic materials, organic electroluminescence materials and the like.

While the invention has been described in detail and with reference to specific examples thereof, it will be apparent to one skilled in the art that various changes and modifications can be made therein without departing from the spirit and scope thereof.

What is claimed is:

1. A process for producing a tetrathiafulvalene derivative precursor represented by formula (1):

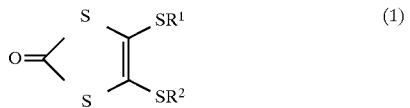

wherein $R^1$ and $R^2$ may be the same or different and represent organic groups that may be linked together to form a ring, said process comprising the steps of:

treating 1,3,4,6-tetrathiapentalene-2,5-dione at a temperature of 30° C. or lower in an alcohol solution containing an alkali metal alkoxide in an inert atmosphere, thereby effecting selective cleavage of one of its rings to form 1,3-dithiol-2-one-4,5-dithiolate dianion; and allowing said 1,3-dithiol-2-one-4,5-dithiolate dianion to react with a compound having a monovalent or divalent organic group which corresponds to said organic groups represented by $R^1$ and $R^2$ in formula (1).

2. A process for producing a tetrathiafulvalene derivative represented by formula (6):

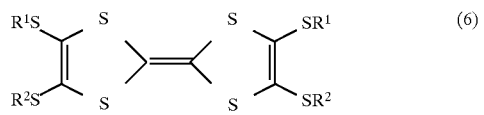

wherein $R^1$ and $R^2$ may be the same or different and represent organic groups that may be linked together to form a ring, said process comprising the steps of:

treating 1,3,4,6-tetrathiapentalene-2,5-dione at a temperature of 30° C. or lower in an alcohol solution containing an alkali metal alkoxide in an inert atmosphere, thereby effecting selective cleavage of one of its rings to form 1,3-dithiol-2-one-4,5-dithiolate dianion;

allowing said 1,3-dithiol-2-one-4,5-dithiolate dianion to react with a compound having a monovalent or divalent organic group which corresponds to said organic groups represented by $R^1$ and $R^2$ in formula (6) to form a tetrathiafulvalene derivative precursor; and heating and stirring said tetrathiafulvalene derivative precursor in the presence of a trialkyl phosphite, thereby effecting coupling of two molecules of said precursor.

3. A process as claimed in claim 1, wherein the temperature for treating the 1,3,4,6-tetrathiapentalene-2,5-dione is from 15 to 30° C.

4. A process as claimed in claim 2, wherein the temperature for treating the 1,3,4,6-tetrathiapentalene-2,5-dione is from 15 to 30° C.

5. A process as claimed in claim 1, wherein the 1,3,4,6-tetrathiapentalene-2,5-dione is treated for a time of about from 5 to 30 minutes.

6. A process as claimed in claim 2, wherein the 1,3,4,6-tetrathiapentalene-2,5-dione is treated for a time of about from 5 to 30 minutes.

7. A process as claimed in claim 1, wherein the inert atmosphere where the 1,3,4,6-tetrathiapentalene-2,5-dione is treated is free from oxygen and moisture.

8. A process as claimed in claim 2, wherein the inert atmosphere where the 1,3,4,6-tetrathiapentalene-2,5-dione is treated is free from oxygen and moisture.

9. A process as claimed in claim 1, wherein the alkali metal alkoxide is present in the alcohol solution in a concentration of about 1M.

10. A process as claimed in claim 2, wherein the alkali metal alkoxide is present in the alcohol solution in a concentration of about 1M.

11. A process as claimed in claim 1, wherein the alkali metal alkoxide is present in an amount of from 1.8 to 2.2 mol per mol of 1,3,4,6-tetrathiapentalene-2,5-dione.

12. A process as claimed in claim 2, wherein the alkali metal alkoxide is present in an amount of from 1.8 to 2.2 mol per mol of 1,3,4,6-tetrathiapentalene-2,5-dione.

13. A process as claimed in claim 1, wherein the alkali metal alkoxide is sodium methoxide, and the alcohol solution is a methanol solution.

14. A process as claimed in claim 2, wherein the alkali metal alkoxide is sodium methoxide, and the alcohol solution is a methanol solution.

* * * * *